United States Patent
Backhaus et al.

(10) Patent No.: US 10,900,009 B2
(45) Date of Patent: *Jan. 26, 2021

(54) METHOD AND DEVICE FOR AUTOMATED REMOVAL OF CELLS AND/OR CELL COLONIES

(71) Applicant: ALS AUTOMATED LAB SOLUTIONS GMBH, Jena (DE)

(72) Inventors: Rafael Backhaus, Cologne (DE); Jens Eberhardt, Gera (DE); Marco Meinhardt, Schmölln (DE); Gerd Bornmann, Weimar (DE)

(73) Assignee: ALS AUTOMATED LAB SOLUTIONS GMBH, Jena (DE)

( * ) Notice: Subject to any disclaimer, the term of this patent is extended or adjusted under 35 U.S.C. 154(b) by 615 days.

This patent is subject to a terminal disclaimer.

(21) Appl. No.: 15/728,937

(22) Filed: Oct. 10, 2017

(65) Prior Publication Data
US 2018/0030397 A1    Feb. 1, 2018

Related U.S. Application Data

(63) Continuation of application No. 12/442,183, filed as application No. PCT/EP2007/059951 on Sep. 20, 2007, now Pat. No. 9,822,331.

(30) Foreign Application Priority Data

Sep. 22, 2006  (DE) .................. 10 2006 045 262

(51) Int. Cl.
C12M 1/26     (2006.01)
C12M 1/36     (2006.01)
C12M 1/00     (2006.01)

(52) U.S. Cl.
CPC ............ C12M 33/04 (2013.01); C12M 41/06 (2013.01); C12M 41/48 (2013.01)

(58) Field of Classification Search
None
See application file for complete search history.

(56) References Cited

U.S. PATENT DOCUMENTS

| | | |
|---|---|---|
| 4,700,298 A | 10/1987 | Palcic et al. |
| 4,907,158 A | 3/1990 | Kettler |
| 5,018,209 A | 5/1991 | Bacus |
| 5,989,835 A | 11/1999 | Dunlay et al. |
| 6,083,762 A | 7/2000 | Papen et al. |
| 6,122,396 A | 9/2000 | King et al. |
| 6,573,039 B1 | 6/2003 | Dunlay et al. |
| 7,382,909 B1 | 6/2008 | Nattkemper et al. |
| 2003/0179916 A1 | 9/2003 | Magnuson et al. |
| 2004/0128102 A1 | 7/2004 | Petty et al. |
| 2005/0026221 A1 | 2/2005 | Richmond et al. |
| 2005/0267690 A1 | 12/2005 | Cong et al. |
| 2006/0256355 A1 | 11/2006 | Karito |
| 2009/0203126 A1 | 8/2009 | Hung |

FOREIGN PATENT DOCUMENTS

| | | |
|---|---|---|
| DE | 19742163 A1 | 4/1999 |
| DE | 102004046740 A1 | 12/2005 |
| DE | 102004027661 A1 | 1/2006 |
| EP | 1502649 A1 | 2/2005 |
| EP | 1754537 A1 | 2/2007 |
| WO | 91/01365 A1 | 2/1991 |
| WO | 00/13609 A | 3/2000 |
| WO | 01/36939 A2 | 5/2001 |
| WO | 02/19594 A | 3/2002 |
| WO | 03/048705 A | 6/2003 |

OTHER PUBLICATIONS

Wang, Zifu, "How to quantify the colocalization in your images?", Developmental Biology Center, University of California, irving, 2006, http://dbc.bio.uci.edu/pdf_documents/Colocalization.pdf, pp. 1-7.

Battye et al., "Single cell Sorting and Cloning", Journal of Immunological Methods, 2000, vol. 243, pp. 25-32.

Brown et al., "Sampling Efficiency of a Single-cell Capillary Electrophoresis System", Cytometry Part A, (published on line Aug. 6, 2007), pp. 882-888.

*Primary Examiner* — Laura Schuberg
(74) *Attorney, Agent, or Firm* — Maier & Maier, PLLC

(57) ABSTRACT

The method comprises an automated removal of cells and/or cell colonies from a cell culture whilst executing a first detection step for selecting cells and/or cell colonies with reference to corporeal and/or physical parameters and detecting position data and storing the detected position data of the selected cells and/or cell colonies in a position database.

In order to be able to select special cells and/or cell colonies having special properties from the detected cells and/or cell colonies, at least one second detection step for detecting at least one further parameter of the cells and/or cell colonies is then executed, comparative data from the data of the first and second detection step are created, cells and/or cell colonies are selected with reference to the comparative data and the position data from the position database are transferred to a harvesting unit.

21 Claims, 8 Drawing Sheets

METHOD AND DEVICE FOR AUTOMATED REMOVAL OF CELLS AND/OR CELL COLONIES

CROSS-REFERENCE TO RELATED APPLICATIONS

This application is a continuation of U.S. application Ser. No. 12/442,183, filed on Mar. 20, 2009, which is the U.S. national stage application which claims priority under 35 U.S.C. § 371 to International Patent Application No. PCT/EP2007/059951, filed on Sep. 20, 2007, which claims priority to German Patent Application No. 10 2006 045 262.3, filed on Sep. 22, 2006, the disclosures of which are incorporated herein by reference in their entireties.

DESCRIPTION

The invention relates to a method and uses of the method for automated removal of cells and/or cell colonies. The invention further relates to a device for carrying out the method.

Within the framework of biological or medical research, work on the care, screening and selection of cells and/or cell colonies in cell cultures has to be carried out with reference to most diverse criteria. At the same time, the cells and/or cell colonies must be specifically selected and transferred into other sample vessels or cell cultures.

The continuously growing market of biotechnology and medical research is presently characterised by the change from largely manual cell culture selection and care towards partially and fully automated systems which select and separate cells with reference to specific criteria. As a result of the very different cell types in this area, having highly varying properties and harvesting behaviour, special solutions adapted to the cell type to be processed are largely produced.

Since in the area of university and also commercial research in this field, the cell lines used are frequently changed due to changing research tasks, the acquisition of these expensive devices having only special uses is of no economic interest for smaller research teams.

So far, the practical implementation has been carried out by taking up various commercially available plastic tips for the removal of particles from media, taking up special plastic tips having an enlarged opening for picking particles from viscous media, taking up metal capillaries for picking strongly adherent particles of different size by scraping or taking up glass capillaries inserted in adapters for separating smaller, non-adherent or barely adherent particles.

Relatively universally usable devices for automation of this work are not available for the separation and culture care of strongly adherent cells and colonies. A major problem is the strong adherence of the cells to the sample vessel. Known methods such as, for example, the targeted cloning by means of enzymes for releasing the binding of the cell membranes from the sample vessel, described in DE 197 42 163 C2 fail due to the time of action of the enzyme before the establishment of the desired effect being too long and due to the cell death and severe reduction in vitality initiated by the damage to the cell membrane caused by the use of the enzyme. Thus, the automation of the targeted selection of such cells is not possible in the known manner. These problems arise particularly in the area of stem cell research.

The practical implementation hitherto has been carried out by means of scraping cannulas made of stainless steel having different diameters, scraping cannulas of glass or metal, which are glued into a conical adapter, or scraping cannulas made of ceramic for smaller diameters.

Due to the mostly high requirements on sterility for protecting the samples from contamination, the cannulas used must usually be changed after each separation cycle. At high throughput this takes place accordingly frequently and is not reasonable manually.

A number of mechanical devices and robot systems are already known for the semi-automatic processing, in particular for the separation, isolation and treatment of cell clones and individual cells.

For example, DE 10 2004 027 661 A1 discloses a drive arrangement for a robot system for isolating and treating cell clones and individual cells. The drive arrangement comprises motor-driven slits which can be moved in two different axial directions and serve to move the separating tool to the samples.

DE 10 2004 046 740 A1 describes a tool head for the automatic isolation and treatment of cell clones. This tool head serves to receive a pipette which in turn receives a cloning dome. A defined force closure between the pipette tip and the cloning dome is possible due to a staggered arrangement of leaf springs.

DE 197 42 163 A1 describes a cloning dome which encloses the cell and/or cell colony during the removal and in which a rinsing process takes place by which means the cell and/or cell colony is released from the vessel. The cell and/or cell colony released by the rinsing is then aspirated through the cloning dome.

An automated method for picking animal cell colonies is disclosed, for example, in EP 1 502 649 A1. The cell culture is scanned with an optical device and image data of the cell culture are produced. These image data are transferred to an image processing unit. In the image processing unit a shape recognition is made using the image data. At the same time, position data of the cell and/or cell colony are detected. The position data thus determined are stored in a position database. The position data are then transferred from the position database to a harvesting unit. The harvesting unit is moved to a spatial location of the cell culture fixed on the carrier according to the previously determined position data. The cell and/or cell colony is then picked by the harvesting unit at the spatial location of the cell culture. A hollow needle in a picking head picks the cell colonies by aspiration from the cell culture. The harvesting unit transports the picked cell and/or cell colony to a destination and deposits the cell and/or cell colony there.

EP 1 754 537 A1 describes a method for selecting and picking animal cell colonies in which the cell colonies are brought into contact with a labelled protein so that the brightness of the cell colonies corresponds to the content of a sought protein. The cell colonies are then selected by means of the brightness.

In the known methods, however, only the positions of cell colonies or cell colonies having specific properties are detected.

It is therefore the object to select cells and/or cell colonies having special properties from the detected cells and/or cell colonies.

The object is achieved with a method for automated removal of cells and/or cell colonies from a cell culture having the features of claim 1 and with a device for the removal of a cell and/or cell colony having the features of claim 27. The dependent claims contain expedient or advantageous embodiments and features of the method or the device.

The method according to the invention comprises an automated removal of cells and/or cell colonies from a cell culture whilst executing a first detection step for selecting cells and/or cell colonies with reference to corporeal and/or physical parameters and detecting position data and storing the detected position data of the selected cells and/or cell colonies in a position database.

Thereafter, at least one second detection step for detecting at least one further parameter of the cells and/or cell colonies is executed, comparative data are created from the data of the second detection step and the data of the first detection step, cells and/or cell colonies are selected by reference to the comparative data and the position data are transferred from the position database to a harvesting unit.

For executing the first detection step during the image processing, corporeal and/or physical parameters, in particular surface areas, sizes and/or outlines and/or spectral parameters, in particular brightnesses and/or fluorescence intensities are detected. Such parameters can be used as standard for identification of the sought cells and/or cell colonies and can be deduced relatively simply from the image points of the detected image information.

The second detection step is introduced for further investigation of the cell and/or cell colony after the scanning and the shape recognition in order to investigate the already identified cells and/or cell colonies with regard to further parameters. During this analysis, no longer the entire scattering plate is scanned but only the regions in which interesting material was found in the shape recognition. This optimises the execution time and in the case of a fluorescence analysis, also the time of illuminating the cell and/or cell colony with fluorescence light, which should be as short as possible to prevent bleaching of the sample.

The basic idea of the invention is therefore, in an automated multi-step process, to locate cells and/or cell colonies having a plurality of specific properties within a cell culture, to select these according to the desired properties, pick them and further process them.

In an expedient embodiment, an xy table is provided as a support for the vessel of the cell culture. In this case, the scanning of the cell culture and the approach of the harvesting unit is executed by a movement of the xy table. In this procedure, the xy-table therefore guides the cell culture gradually along under an image acquisition unit through individual coordinate points, wherein a series of images is recorded and processed. The identified locations are then approached in a corresponding manner by the harvesting unit so that the xy-table displaces the cell culture in relation to the harvesting unit such that this is located above the corresponding coordinate position. As a result, expensive displacement and adjusting mechanisms for image acquisition and harvesting unit are saved and only one adjusting device is required for both process sections.

Preferably, partial images of the cell culture are recorded during scanning and the first and/or second detection step are carried with reference to the partial images. This constitutes a major advantage with regard to the required image storage device and the image quality during detection. The image recognition can additionally be made on unchanged image data on the software side and therefore on the physically best-possible resolution and image fidelity. It is possible to work with full resolution at the set magnification whereas when analysing the combined image, which is described further below, zooming in closer is usually used in order to keep the quantity of image data within the frame.

Alternatively to this, an entirety of the partial images covering the cell culture is expediently recorded during the scanning process step. In this case, the image data of the partial images is combined in an image processing unit to form image data of an overview image of the cell culture. Such a procedure is expedient because under the conditions of a microscopic imaging, only one section of the cell culture can be detected but on the other hand, the absolute position of a cell or cell colony in the area of the cell culture must be known for the subsequent removal. Under these conditions, the overview image of the cell culture necessarily consists of a mosaic of partial images.

During the detection of the position data, a determination of the shape centre of gravity of identified forms is made. In this case, the coordinates of the shape centre of gravity are stored as the position data for the identified shape in the position database. For a detected shape or contour this expedient procedure defines its position with a relatively small data volume. In this case, the image points pertaining to one shape are combined to form a reference image point which specifies the position of the determined cell or cell colony.

The shape recognition and the detection of the position data expediently include a determination of distances between the identified forms. Due to this embodiment of the method, it can be specified inter alia which detected cell or cell colony still pertains to a detected group or should be removed individually. In this case, in particular, the range with which cells or cell colonies in the vicinity of the determined position data can be removed with a single access can be taken into account for a given harvesting tool. More remotely located cells or cell colonies must then be approached separately.

During the scanning, the shape recognition and/or the detection of the position data, a real-time display of the image data is expediently made on a monitor. By this means the entire procedure can be monitored and influenced if necessary.

The second detection step preferably consists of arbitrarily many individual steps in which various parameters are detected and the parameters in the individual steps are recorded with different types of exposure. Thus, in the second detection step, many different fluorescence channels and excitation wavelengths can be scanned and evaluated. In this case, the software merely collects particle data which are less data-intensive than image data.

In an advantageous embodiment of the invention, the selection of the cells and/or cell colonies is made by reference to corporeal and/or physical parameters by means of a first interactive selection list. The selection of cells and/or cell colonies is made by reference to comparative data by means of a second interactive selection list or an interactive scatter diagram. In the scatter diagram two different particle values are imaged with respect to one another from the result list. An automated selection of the cells and/or cell colonies is possible due to the interactive selection lists or the interactive scatter diagram.

The first interactive selection list preferably contains at least coordinates of the shape centres of gravity and image data and/or data from the first detection step. The second interactive selection list contains at least the data from the first selection list and the second detection step and/or the comparative data. With the aid of the selection lists, it is possible to view the position database manually and check and select the cells or cell colonies which have been found automatically. As a result, selection errors can be corrected. In addition, the storage of these data is less complex compared with the storage of image data.

The selection of the cells and/or cell colonies is preferably made by logic filters. The cells and/or cell colonies can thereby be filtered logically by means of the presence or absence of individual fluorescence or bright field signals.

The picking of cells and/or cell colonies in an adherent cell culture, i.e. adhering to the bottom of a container, takes place with the following expedient steps: firstly, a tip is taken up and the tip is filled with an enzyme or solvent. Then, a cloning dome is taken up and a cell and/or cell colony is enclosed by the cloning dome. The enzyme or solvent contained in the tip is then dispensed from the tip into an interior of the cloning dome. The cloning dome is rinsed, thereby releasing the cell and/or cell colony. The cell and/or the cell colony is now aspirated.

In a strongly adherent cell culture the picking of a cell and/or the cell colony takes place with the following expedient steps:

Firstly, the cell and/or cell colony is enclosed with a tip of a cannula. Then, a relative movement of the cannula tip is executed in the xy plane and the cell and/or cell colony is scraped off. The scraped-off cell and/or cell colony is then picked into the cannula. Such a procedure is recommended when the cell or the cell colony adheres strongly to its base and release by a solvent or an enzyme would severely increase the risk of destruction or damage to the cell or cell colony.

In an alternative embodiment, the relative movement of the cannula tip and/or the xy table is combined with an aspiration and/or rinsing process in the cannula tip. This is particularly advantageous when stem cells are to be picked.

If the desired determined cell and/or colony and/or partial region of a colony is enclosed by a cannula tube and released from the bottom of the sample vessel by relative movements of the tool and/or the sample vessel on the cross-table and picked into the cannula, corresponding cells and/or colonies can be separated in a substantially shorter time and substantially more gently compared to the conventional method. Frequently, automation of these processes for specific types of cells is possible for the first time by using this method.

A principal area of application of this new type of technology for separating strongly adherent cells is research in the field of animal and human stem cells. The targeted release from regions of solid cell groups (cell lawns) is also possible by this method.

The targeted separation of partial regions of a cell colony (e.g. undifferentiated stem cells which are surrounded by already-differentiated stem cells) is thereby possible in an automated manner.

Compared with conventional oscillating methods, the aforesaid scraping method furthermore has the advantage that the undesirable uncontrolled release of individual cells from the colony group due to the oscillating barely arises. The structure of the colony to be harvested remains largely preserved.

The following steps are expediently carried out for picking of a cell and/or cell colony from a semisolid nutrient substrate, in particular agar or methyl cellulose:

Firstly, a tip is taken up. The tip is then positioned over the cell and/or the cell colony and the cell and/or cell colony is enclosed by the tip. The cell and/or cell colony and the nutrient substrate in the vicinity of the cell and/or the cell colony is then aspirated into the tip.

Positionally fixed individual cells are expediently picked with the following steps:

In a first step, a capillary is filled with a fluid, in particular air or a liquid in a calibrated quantity. The capillary opening is positioned above an individual cell and/or individual colony. The medium in the vicinity of the individual cell and/or individual colony is aspirated into the capillary, wherein the individual cell and/or individual cell colony is picked into the capillary.

In an expedient variant, the filling of the capillary with the calibrated quantity of fluid is accompanied by an image acquisition of the capillary in conjunction with an image data evaluation in an image processing unit.

A cell colony whose size exceeds the usable diameter of the tip, the cannula or the capillary, is preferably harvested successively in parts. In this way, relatively large cell colonies can also be harvested.

Alternatively, individual parts are separated out from a cell colony with the aid of the tip, the cannula or the capillary. In this way, regions of a cell colony having specified properties can be harvested separately from other regions. Such a method is particularly suitable for the harvesting of undifferentiated stem cells surrounded by differentiated stem cells.

In a further alternative embodiment, individual regions are separated out from solid cell groups. In this way, specified regions having desired properties can be separated from regions having undesired properties.

The cells and/or cell colonies sorted by settling are preferably deposited in a depositing container and the position data of the deposited cell and/or cell colony are detected and processed. It is thus possible for harvested cells and/or cell colonies to be deposited in the depositing container sorted according to classes (density, fluorescence etc.), which can be valuable for downstream processes. In addition, after each harvesting process, the image processing software receives the information as to which container and at which position in this container the robot controller has deposited the cell and/or cell colony, thus ensuring a complete logging of the entire process.

The method is preferably used for removing stem cells, biological and/or chemical particles or solids, in particular beads.

A device for removing a cell and/or a cell colony from a cell culture is characterised by a microscope unit for microscopic scanning of the cell culture in combination with an image acquisition unit and an image evaluation unit for detecting the position of the cells and/or the cell colonies in the cell culture, a control and memory unit for storing the detected position of the cell and/or cell colony and a harvesting module having a removal tool for removing the cell and/or cell colony at the detected position of the cell and/or cell colony.

The provision of a device according to the invention should indicate a way in which a plurality of completely different cell types can be processed with a single device. For this purpose, it is possible to equip the modular device with different tools and software sequences.

These devices having a drive device according to DE 10 2004 027 661 and having the cell-typical removal heads used in the tool head according to DE 10 2004 046 740 are capable of implementing the various methods used for automated cell harvesting for separating a wide range of individual cells and cell colonies.

In these methods, capillaries having different sizes, shapes and materials are usually used for releasing and/or picking the clone or particle.

By implementing largely standard adapters for these different forms of cannula, it is possible to use largely the same tools for a wide range of applications which brings about a high cost efficiency and a drastic reduction in development expenditure and development time.

In one embodiment of the device, the removal tool consists of a tip which can be filled with a dissolving or enzymatic liquid, a cloning dome which can be coupled to the tip, which covers selected cells and/or cell colonies and which can be filled with the liquid contained inside the tip, as well as a loading and aspiration device for the tip and the cloning dome.

In a further embodiment, a removal tool is provided in the form of a magazine having an arrangement of cannulas of different diameters mounted inside the magazine, and a coupling unit for automatic removal of the cannulas from the magazine and the integration thereof in an exchangeable head.

The cannulas are preferably formed in different sizes, shapes and/or materials. It is thereby possible to adapt to the properties of the cells and/or cell colonies to be harvested.

These and other methods in future can be implemented by supplementing the range of usable cannulas whereby more extensive applications can be developed without major technical development expenditure by slight mechanical modifications to the tool head and adaptations in the sequence software.

In a further embodiment, a removal tool having a suction tip with an enlarged cross-section in its tip section is provided.

Finally, in a removal tool in a further expedient embodiment, a cannula, an image recording device for monitoring a quantity of fluid contained in the cannula, an image processing device for processing the image information of the cannula and a suction device for aspirating cells and/or cell colonies into the cannula are provided.

The method and the device will now be explained in detail hereinafter with reference to exemplary embodiments. The appended figures serve for illustration. The same reference numerals are used for parts or process steps which are the same or which have the same effect. In the figures.

Figure 3:
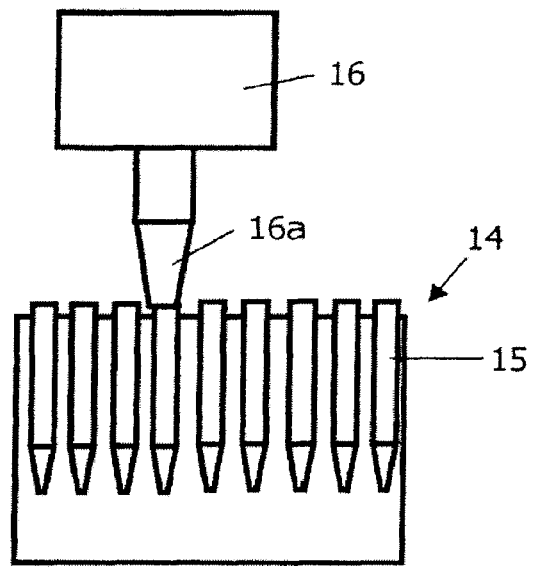
Figure 4:
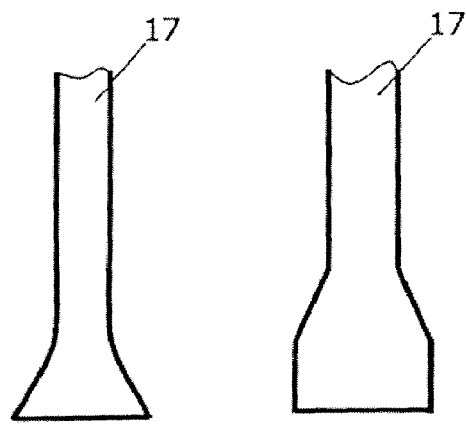
Figure 5:
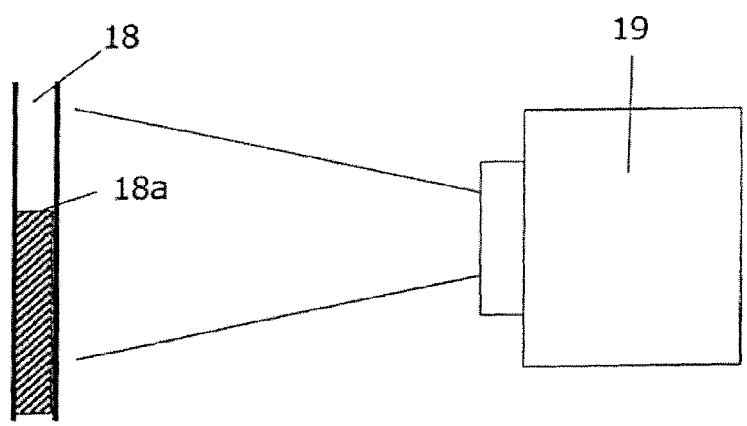
Figure 6:
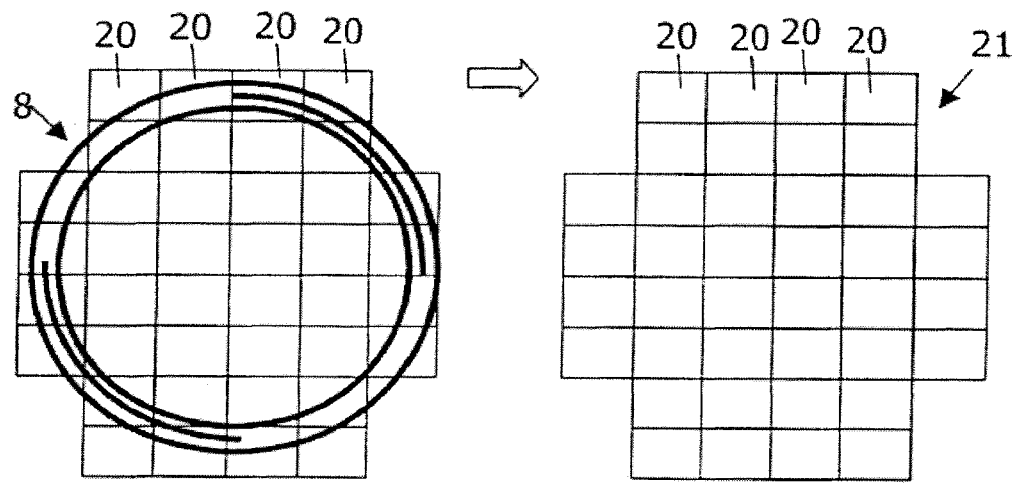
Figure 7:
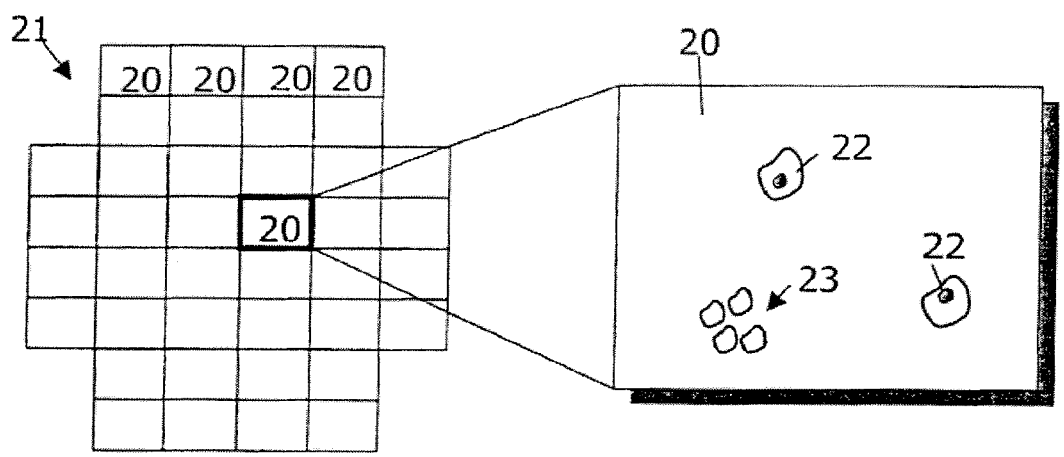
Figure 8:
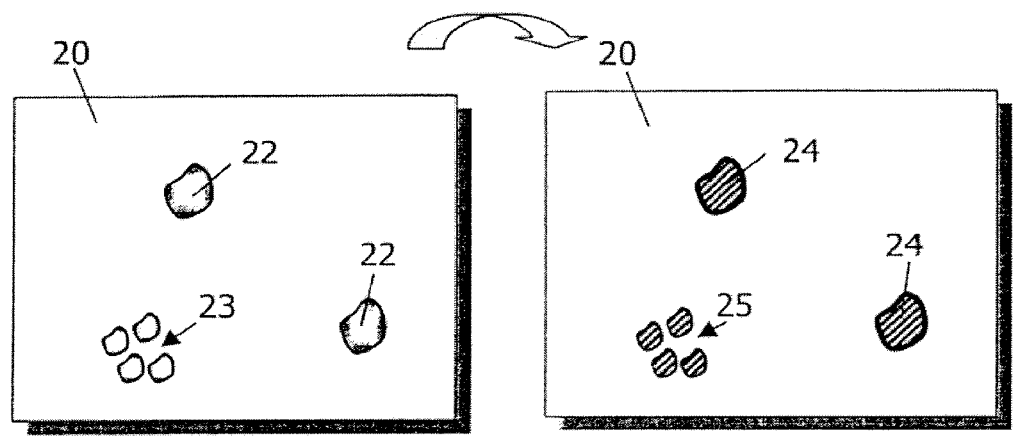
Figure 9:
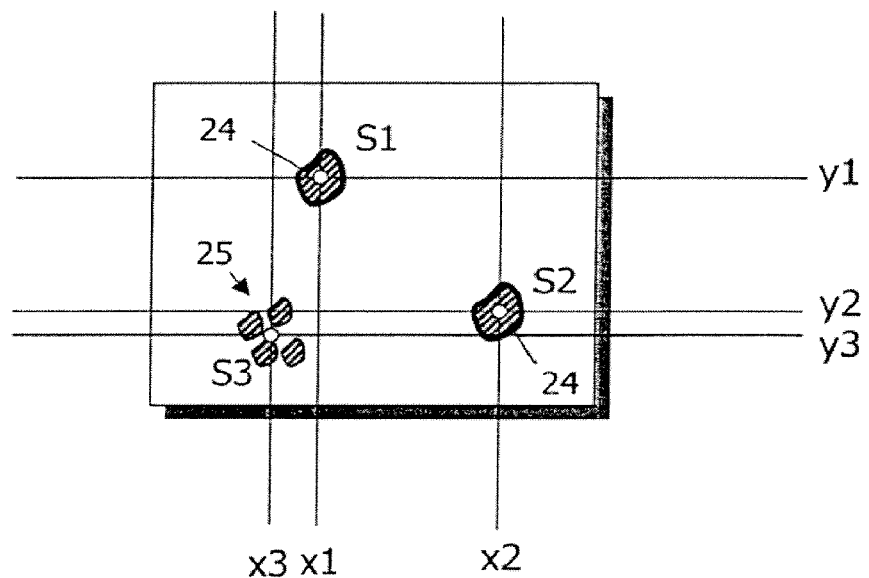
Figure 10:
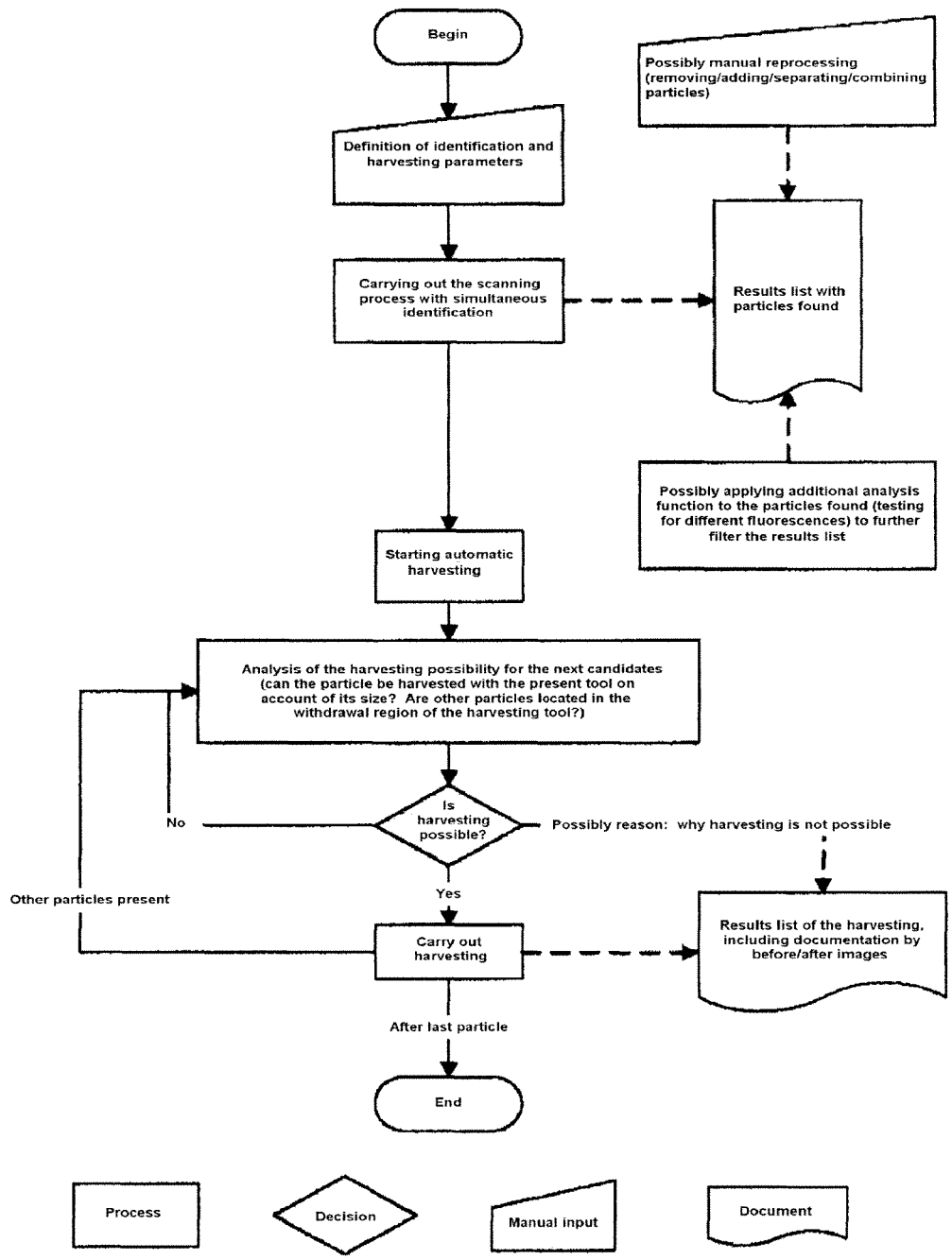

FIG. 3 shows an exemplary cannula magazine comprising a number of cannulas and a tool head with an adapter, FIG. 4 shows two embodiments of an exemplary suction tip with enlarged cross-sections in the tip region, FIG. 5 shows an exemplary capillary with an image recording device for calibration, FIG. 6 shows a first process step comprising recording partial images and combining the partial images to form an overview image, FIG. 7 shows an exemplary selected partial images with cells and a cell colony, FIG. 8 shows a schematic shape recognition of selected cells and cell colonies, FIG. 9 shows schematic shape centres of gravity and position coordinates of the identified cells and cell colonies and FIG. 10 shows an exemplary flow diagram of the fundamental sequence of automatic cell harvesting using the device.

Figure 11:
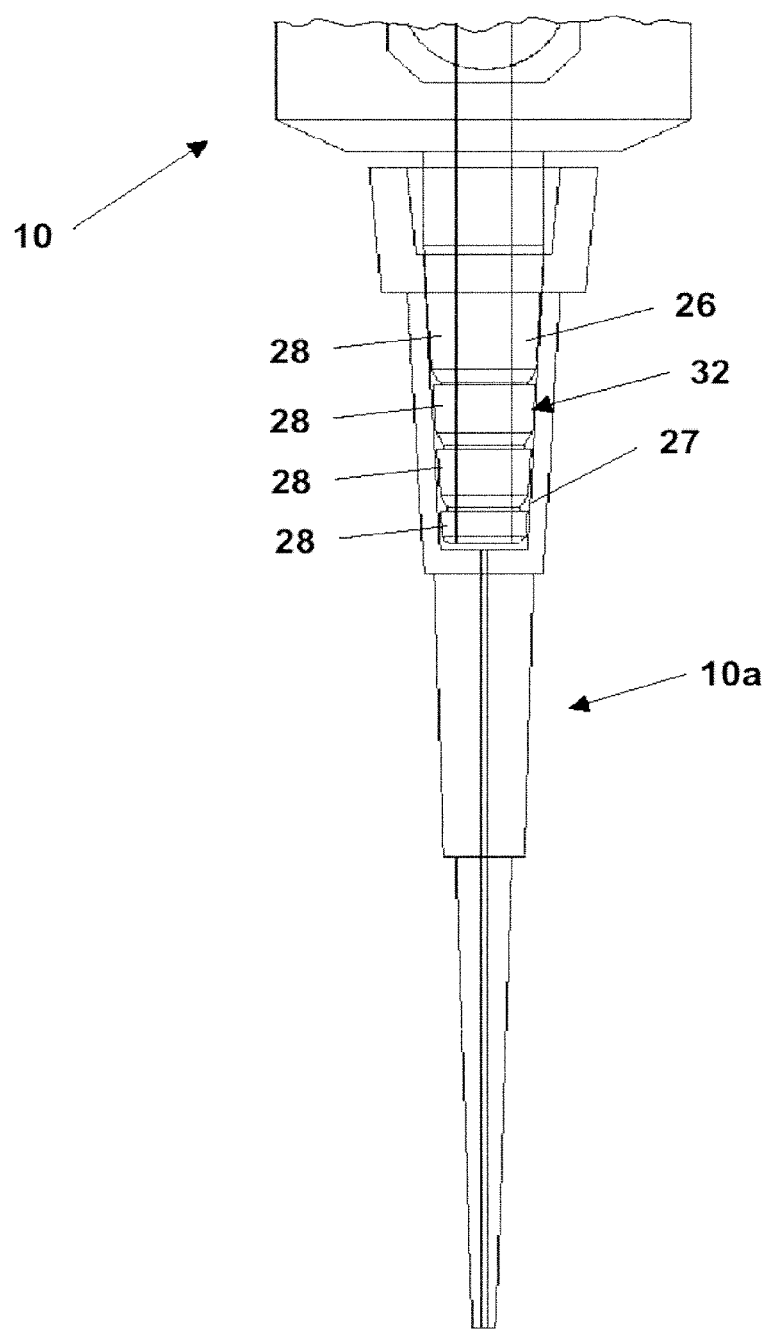

FIG. 11 shows an exemplary embodiment of a receptacle which may be attached to a tool head of the device.

Figure 12:
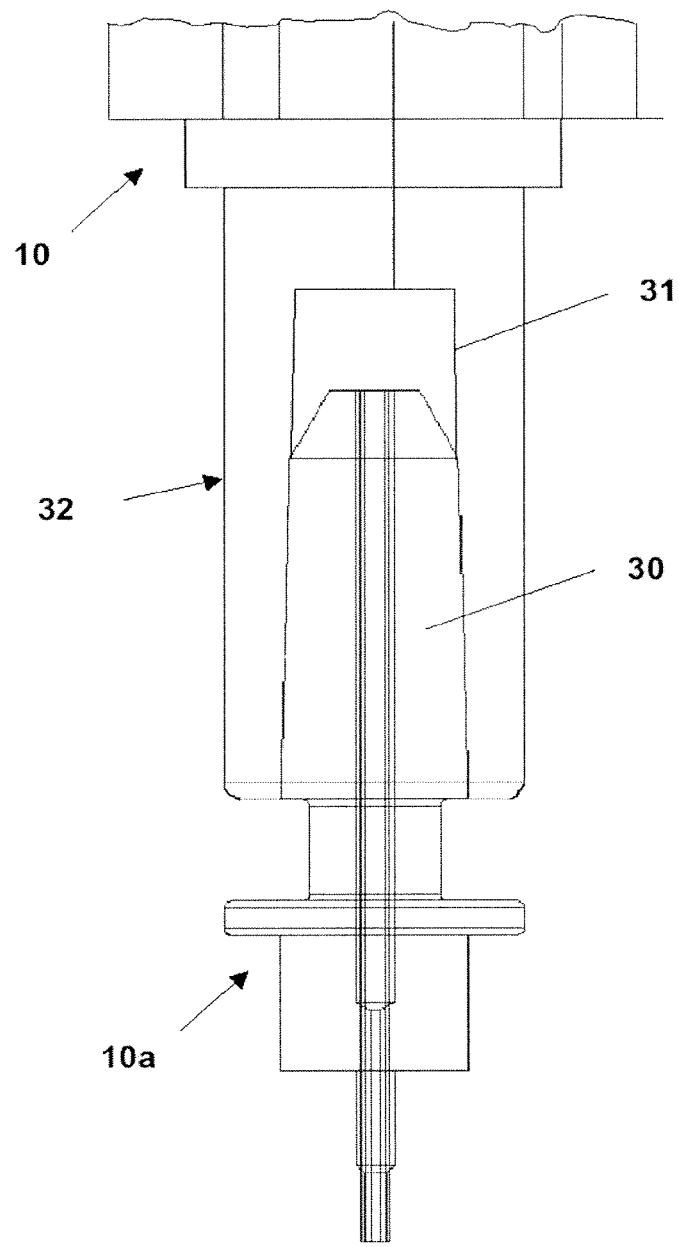

FIG. 12 shows an alternative exemplary embodiment of a receptacle.

Figure 1:
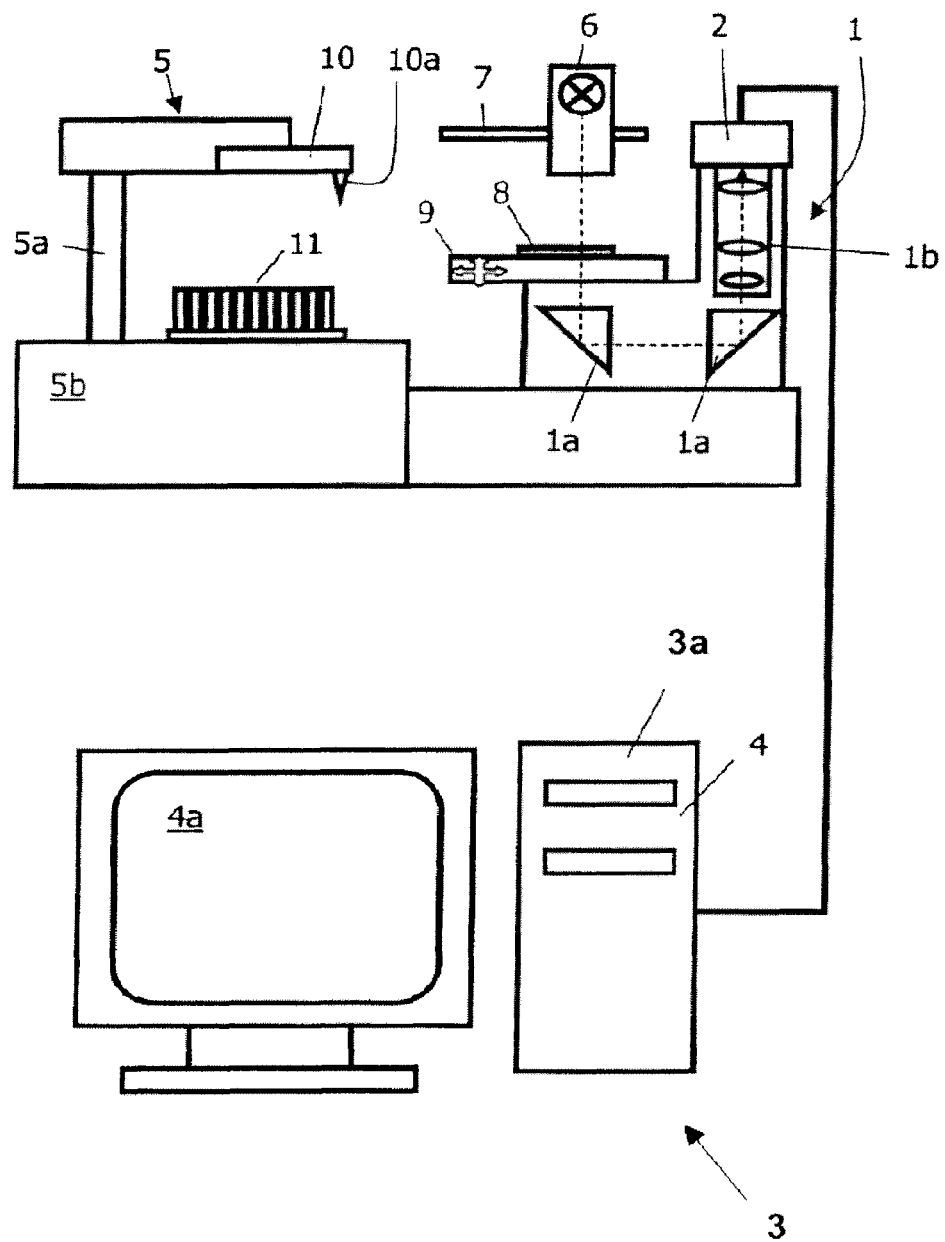
FIG. 1 shows a device for implementing the method in one exemplary embodiment.

FIG. 1 shows an exemplary embodiment of a device for removing a cell and/or cell culture. The device includes a microscope unit 1 with a number of optical components, in particular an arrangement comprising deflecting prisms 1a and a lens system 1b for beam guidance and microscopic imaging. The microscope unit 1 is coupled to an image recording unit 2, usually a CCD camera or a CCD array. An image evaluation unit 3a is provided for processing the image information read out from the image recording unit 2. The image processing unit 3a consists of a personal computer 3 with image processing software running thereon. A control and storage unit 4 is furthermore provided, which is integrated in the personal computer 3 and whose functions are implemented by further software components. The control and storage unit 4 comprises a monitor or a display 4a.

The device furthermore contains a harvesting module 5 which is mounted on a displacement mechanism. The displacement mechanism consists of a lifting column 5a and a displacement drive 5b. The lifting column 5a and the displacement drive 5b are designed for larger displacement distances and are used for bringing a harvesting module 5 towards a cell culture 8 located in a sample container, coarse adjustment of the harvesting module 5 and movement of a removal tool 10a towards the corresponding separating stations of the removed cells and/or cell colonies.

The aforementioned microscope unit 1 is configured as a transmission microscope. For this purpose, illumination 6 with a series of switchable illumination filters 7 is provided. The illumination 6 transilluminates the cell culture 8 located in the sample container. The cell culture 8 is fixed on a support in the form of an xy-table 9 by which means the cell culture 8 can be moved with a microscopic adjustment accuracy of a few micrometers both in the x and in the y direction below the optical arrangement consisting of illumination 6 and deflecting prism 1a located thereunder. In this case, the adjusting coordinates of the xy table 9 are transmitted to the storage and control unit 4 or adjusted by the storage and control unit 4.

The microscope unit 1 consists of a commercially available microscope stand which is equipped with a motorised xy table 9. Optionally, this microscope unit 1 can also be equipped with a commercially available fluorescence device. The fluorescence device can accommodate up to 3 filter cubes (consisting of excitation filter, dichroic mirror and emission filter) and can be illuminated either by means of a commercially available gas burner or by means of external illumination 6 which is coupled in with glass fibres. It is also possible to place the emission filter into a motorised filter wheel before the illumination 6 in order to then simultaneously scan fluorescences with corresponding triple or quad-band filter cubes in the fluorescence device. In addition, the image recording unit 2 with CCD chip is mounted on the microscope unit 1 by which means scanning of the sample is possible. By using commercially available phase contrast sliders, physically optimum phase contrast illumination is possible.

The commercially available PC is connected to the basic device via a network connection. Running on this is commercially available standard image processing software, which together with a specially programmed robot controller and specially developed modules for this image processing software, takes over the driving of the device and the analysis of the image data.

As will be explained in detail subsequently, in conjunction with the movement of the xy table 9, the entire area of the cell culture is scanned, whereby a number of microscopic individual images of the cell culture are recorded by the image detection unit.

The movement of the xy table also serves to position the cell culture for the removal of the identified cells or cell colonies. For this purpose, the harvesting module 5 is positioned by the displacement mechanism above the cell culture 8 whilst the xy table is adjusted to the previously determined positions of the identified cells and cell colonies and enables the harvesting module 5 to remove the cells or cell colonies.

The removal of the cells or cell colonies from the cell culture 8 located in the sample container requires a lowering of a removal tool 10a into the cell culture 8, a picking of the cells or cell colony and their separation. For this purpose, the removal module 5 has a tool head 10 which is fitted with a lowering or suction mechanism. The removal tool 10a is located at the end thereof. The picked cells or cell colonies are deposited in a separating battery 11. This consists of a row of test tubes or tubes which can be driven individually by the lifting column and the displacement drive and in which the removed cells and cell colonies can be deposited by the tool head.

In addition, the separating battery can also be configured in parts as a magazine for the preparation of removal tools 10a which can be coupled onto the tool head 10 as desired, as will be explained in detail subsequently.

In principle, the functions described here in principle are controlled by the storage and control unit 4 and run substantially fully automatically. However, due to the monitoring of the functions on the monitor or display, the user has a number of possibilities for influencing the function by the known input means such as keypad and mouse and a corresponding user interface at the software components running inside the storage and control device.

Thus, in particular, an adjustment of the magnification factor and a change in the resolving power of the image recording device are possible by access to the control of the microscope device. Furthermore, by controlling the illumination and the illumination filters, spectral ranges can be modified or the microscope device can be switched to fluorescence or dark field operation.

Furthermore, it is possible to address the harvesting module 5 whereby individual cells or cell colonies determined by the microscope unit can be selected in a menu-controlled manner and allocated to a specified place in the separating battery 11. In addition, an operating mode of the harvesting module can be selected in which, depending on the selected cells or cell colonies, specified removal tools 10a can be taken from the conical receptacle 32 of the tool head 10 in order to remove the selected cells in a certain manner.

From this point, according to the separation method selected in each case, different removal tools 10a now come into action which can separate the particles and transfer them into a corresponding target container with the aid of different cannulas 15, 18 and/or capillaries and different sequences. These methods are described in detail hereinafter.

The removal tool 10a sits at the upper end of the drive arrangement and can be changed freely according to the application. Five different removal tools 10a can be used for the applications "adherent cell colony harvesting with enzyme", "adherent cell colony harvesting without enzyme by scraping", "harvesting from agar", "harvesting from methyl cellulose" and "harvesting from positionally fixed individual cells". All these removal tools 10a have in common that the application-specific software part is mounted directly in the removal tool 10a so that when the removal tool 10a is put in place, the PC software automatically executes the correct application and brings the correct consumables to the feed receptacle. For the structure used in some of the removing tools 10a as tool head 10 reference is made to DE 10 2004 046 740. The description of the aforesaid individual applications is made hereinafter.

All the applications have in common that the scanning and analysis process takes place in the same way. The process only differs according to the application and therefore according to the removal tool 10a used during the harvesting or picking of the particles.

Harvesting of Adherent Cell Colonies by Means of Enzyme:

This method is used for the complete or partial detachment of cell colonies which adhere to the bottom of sample containers (with these types of cells, the adhesion is necessary for the survival of the cells and their multiplication).

Following the process steps of scanning and detection of the objects of interest for the user, described further below, these are positioned for harvesting. The tool head according to DE 10 2004 046 740 is prepared for harvesting by first taking up a commercially available tip 12 made of plastic and filling this tip 12 with an enzyme or solvent (possibly temperature-controlled) optimised for the respective cell type in order to then take up a cloning cup 13 according to DE 197 42 163 C2. The colony to be separated is enclosed with this cloning cup 13 and by dispensing the enzyme or the solvent from the tip 12 into the interior of the cloning cup 13 and therefore onto the object concerned, corresponding rinsing cycles and times of action and finally taking up the volume inside the cloning cup 13 into the tip 12, the desired colony is separated from the sample container and can then be transferred into another sample container and further processed and investigated there.

Figure 2:
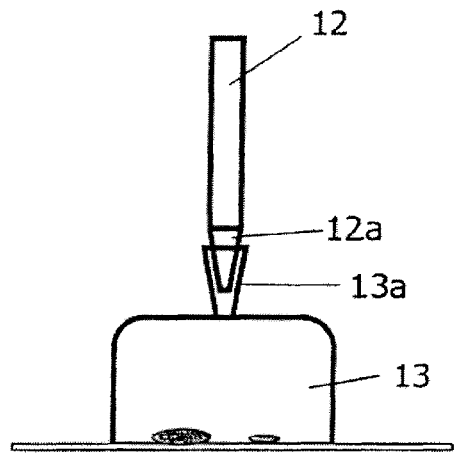
FIG. 2 shows an exemplary removal tool comprising a tip and a cloning dome.

FIG. 2 shows a first removal tool 10a for this purpose. A tip 12 which can be filled with liquid, in particular a solvent or an enzyme, is combined with a cloning cup 13. The tip 12 shown here comprises a tubular structure in the form of a pipette or cannula which has an end cone 12a which is inserted in a receiving cone 13a of the cloning cup 12 and engages positively there. The tip 12 is expediently first filled with liquid and receives the cloning cup 13 outside the cell culture 8. The combination of tip 12 and cloning cup 13 thus formed is placed over the selected cells or cell colonies in the cell culture 8. The liquid is then dispensed inside the tip 12 into the cloning cup 13. The cells thereby detached are then aspirated from the cloning cup 13 into the tip 12. Such a removal tool 10a is particularly suitable for adherent cells and cell colonies, i.e. those adhering to the bottom of a vessel. The cloning cup 13 thereby covers a region of the cell culture 8 stipulated by its radius. The radius of the cloning cup 13 should be selected in this case depending on the density of the cell population. A particular advantage of the cloning cup 13 is that the relative positioning between removal tool 10a and cell culture 8 which is executed by means of the xy table 9 as mentioned, can be carried out with comparatively limited accuracy.

A mechanical detachment of the cells can also be used for the removal of adherent cells and cell colonies for which experience shows that damage to the cell structures occurs under the action of enzymes or solvents. For this purpose, the selected cells or cell colonies are enclosed by the tip of a cannula 15 and released from the base by scraping as a result of a relative movement of cannula 15 and vessel. Depending on the application or adherence strength, the cannula 15 consists of various materials, for example, glass, plastic or metal and has different inside diameters, wherein a plurality of cannulas 15 in different designs can be held in readiness in one magazine.

According to the requirements for sterility and throughput, the cannula 15 can be changed manually or automatically. A cannula magazine 14 is used for automatically changing the cannula 15. FIG. 3 shows a cannula magazine 14 with a number of cannulas 15 located therein. This arrangement can be configured as a part of the separating magazine 11 shown in FIG. 1, reserved particularly for this purpose. An interchangeable head 16 provided for this purpose has an adapter 16a for grasping and withdrawing a cannula 15 from the cannula magazine 14.

An interchangeable head 16 is moved over the cannula 15 and lowered. This grips the cannula 15 and moves this over the cell culture. A displacement of the xy table 9 to the position of the selected cell or cell colony takes place there. The cannula 15 is lowered and encloses the cell. The xy table 9 now executes slow oscillating movements whereby a negative pressure is produced in the cannula 15 which aspirates the cell.

Harvesting of Strongly Adherent Cell Colonies (Stem Cells, Cells on Feeder Cells, Etc) by Mechanical Action:

This method is used for the complete or partial detachment of cell colonies which adhere strongly to the bottom of sample containers (with these types of cells, the adhesion is necessary for the survival of the cells and their multiplication).

The tool head 10 according to DE 2004 046 740 differs from the previously explained tool head 10 by using a cannula 15 as removal tool 10a. Depending on the application, the cannula 15 can consist of different materials (plastic, glass, metal) and have different inside and outside diameters depending on the size of the colonies to be harvested. Depending on the requirements for sterility and throughput, the cannula 15 can be changed manually (usually combined with a disinfection step between the harvesting processes) or automatically (special cannulas 15 are provided in racks similar to the tips 17).

Following the process steps of scanning and detection of the objects of interest for the user, described further below, these objects are positioned for harvesting. The colony to be separated is enclosed with the cannula 15 (the end of the cannula lies on the bottom of the sample vessel). The detachment of the strongly adherent colony is effected manually, by relative movements of the cannula 15 (scraping and therefore displacement of the enclosed colony on the bottom of the vessel), possibly in combination with aspiration and rinsing processes of the syringe.

The relative movement is produced by moving the xy table 9, the removal tool 10a or both in combination. The additional use of cell-dissolving enzymes inside the cannula 15 is also possible.

After detachment of the colony, this is taken up in the cannula 15 and transferred to another container. The cannula 15 is now disinfected depending on the application or a new cannula 15 is taken up. The next colony can then be harvested.

This tool head 16 with cannulas 15 was produced after problems had arisen during the detachment and the time required for this in the case of the aforesaid tool head 10 with tip 12 for harvesting adherent cells by means of enzyme for various cell types. The enzymes for detachment of the cells attack the cell membrane. A too-high dosage or too-long time of action of the enzyme, as is required for strongly adherent cells, frequently leads to damage or destruction of the cells. However, the main applications of the device lie in the separation of living cells which are to be further cultivated and multiplied after harvesting. Thus, a new automatable method was required for these cell types in order to be able to separate these strongly adherent cells.

By using cannulas 15 of different diameters and materials with flat ends and a conical adapter according to DE 10 2004 046 740 which makes it possible to take up, dispense and magazine the cannulas 15, and with the aid of corresponding devices having automatic sequences as well as tool heads 10 for picking up the cannulas 15 according to DE 10 2004 046 740, harvesting could be carried out successfully on strongly adherent cell types.

In addition to the use of cannulas 15, the use of relative movements for the gentle detachment of individual cells and/or colonies is a further feature of the invention. The relative movement is either executed by the cannula 15 (movement of the removal tool), the sample (movement of the xy table 9) or both. Direction, travel and speed are determined according to the respective cell type.

The selection of the diameters of the cannulas 15 is made with reference to the size of the cells and/or colonies to be separated. By using the conical receptacle 32 as adapter (see Patent Application DE 10 2004 046 740), these highly varying cannula sizes and materials can be handled with the same tool. Special cannulas 15, primarily of smaller diameter or non-metallic materials—can be glued into corresponding conical adapters.

After depositing the cell in the separating magazine 11 and an optional disinfection process, the cannula 15 can now be deposited in the cannula magazine 14 and a new cannula 15 removed.

The method is described hereinafter with reference to feeder cells:

The harvesting of colonies of feeder cells with picking of feeder cells is effected by means of a scrape module. The colony is completely enclosed by a metal capillary of the scrape module or a part of the colony is stamped out by the metal capillary. For this purpose, the metal capillary is placed on the bottom of the culture dish during harvesting. Feeder cells surrounding the colony or feeder cells located under the colony are detached and picked by means of a scrape movement. They are deposited in the target well. This is usually not perturbing since the feeder cells no longer divide and die after some time.

The harvesting of colonies of feeder cells without picking feeder cells is effected with the glass capillary. For this purpose, the upper region of the colony is picked by means of aspiration at a distance of 0-50 gm above the target colony.

Since the colony is a three-dimensional object, the aspiration forces only act on the upper region of the colony facing away from the bottom of the dish and not on the edge zones or regions outside the colony. The size and depth of the piece to be picked is thereby specified by the diameter of the capillary, the distance from the colony, the amount of aspiration and the aspiration speed and must be determined empirically for each cell type. As a result, only cells or a part of the colony are harvested without the surrounding feeder cells or those located thereunder. It is furthermore possible to harvest several clonal (genetically identical) pieces of a colony by repeated picking at the same location. For this purpose, the distance of the capillary tip from the colony must be re-adjusted each time to always produce the same aspiration force.

Harvesting of Colonies from Semi-Solid Nutrient Substrates (Agar, Methyl Cellulose):

This method is used for the complete or partial removal of cell colonies located on the base or inside the nutrient media.

Following the process steps of scanning and detection of the objects of interest for the user, described further below, these are positioned for harvesting. The tool head 10 according to DE 10 2004 046 740 is prepared for harvesting by picking up a special plastic tip 17 which is characterised by a larger inside diameter at its tip in relation to its picking volume compared with commercially available plastic tips (was previously shortened). This tip 17 is positioned over the colony to be separated or the colony is enclosed by said tip. By aspirating the nutrient medium in the vicinity of the colony or the included content of the special tip 17, the colonies are taken up with the nutrient medium and can then be transferred to another sample container and further processed and studied.

Agar:

When harvesting from agar, insertion into the colony surrounded by the agar is frequently sufficient so that particles adhere to the tip 17 of the removal tool 10a and this is then rinsed off in the target well which is filled with nutrient medium. A special tool for this application then requires n syringe drive for aspirating the particles.

FIG. 4 shows two exemplary tips 17 with apexes having an expanded inside diameter for removing cells from semi-solid nutrient substrates, especially agar or methyl cellulose. The tip 17 expediently consists of glass or plastic. It is positioned over the previously selected cell and lowered, whereby the cell or cell colony is enclosed in the apex of the tip. The nutrient medium together with the cell or cell colony contained therein is then picked up by means of the expanded tip and can be transferred to the separating magazine.

Harvesting of Positionally Fixed Individual Cells:

This method is used for removing individual cells or small cell colonies which are located on the bottom of the sample container and remain largely positionally fixed there but exhibit no or only minimal adherence.

Following the process steps of scanning and detection of the objects of interest for the user, described further below, these objects are positioned for harvesting. The tool head 10 according to DE 10 2004 046 740, however, does not take up a plastic tip for this application but a capillary. This is filled with air or a fluid via the connected syringe drive depending on the cell type and application requirements, calibrated by means of image processing and thus prepared for the harvesting process.

The capillary opening (different diameters depending on cell and colony size) is positioned over the cell or colony to be separated. By aspirating the nutrient medium or buffer in the vicinity of the individual cell or colony, the desired cell or colony is picked up with the medium and can then be transferred to another sample container and further processed and investigated.

FIG. 5 shows a cannula 18 for removing positionally fixed individual cells. Such a cannula 18 is suitable for removing individual cells or cell colonies which are located on the bottom of a sample container and remain there in a positionally fixed manner but not adherently. This is filled with air or a fluid, the fluid level 18a of the cannula 18 being recorded by an image acquisition system 19 and calibrated. For removal of the cell or cell colony, the opening of the cannula 18 is positioned over the cell or cell colony. By aspiration of the nutrient medium or buffer over the cell, these together with the medium enters into the interior of the cannula 18 and can then be transferred. In this case, the diameter of the cannula opening must be adapted to the sizes of the cells.

This and in future other methods can be implemented by supplementing the base platform of the device and its axial system according to DE 2004 027 661 and using complete microscope optics.

The process of cell detection and image processing will be explained in detail in the following.

Firstly the user loads the feed receptacle with corresponding target plates, consumables and liquids and equips the microscope cross table with its starting plate in which the cell cultures to be harvested are located. These plates can be freely defined and calibrated in the image processing software. These plates can then be scanned.

For scanning the table is moved in a pattern which corresponds to the image section of the optical camera system. The content of the complete plate can thus be scanned image by image. After one of these individual images has been scanned, a particle detection takes place immediately based on grey threshold values (and therefore on brightness differences). Corresponding mathematical filters can be used before this detection in order, for example, to optimise contrast or prepare the image for better detection. This detection is made image by image, i.e. during scanning. In this case, edge-overlapping particles are automatically identified by the software and combined to form one particle. This type of detection is therefore also designated as edge-overlapping detection. As a result, primarily only a so-called particle map remains which shows in binary form where identified particles are located and where not. Thus, image data need not be held expensively in the memory but merely a map of the detection result. Optionally, a reduced-size overview image can be produced and stored. In addition to the already-mentioned filters for image processing, further filters can be used after the detection. Thus, the identified particles can be evaluated and filtered out with regard to their morphological (shape, size etc.) and qualitative parameters (density, brightness differences etc.). This procedure has the advantage that the analysis of the particles is made by reference to the individual images recorded with 100% resolution, not with a possibly quality-reduced overview image.

All the remaining particles are output to a particle list and can be individually approached, evaluated and reprocessed by the user.

FIG. 6 shows schematically the cell culture 8 in the left-hand partial image. By means of a movement of the xy table 9, the cell culture is scanned with a series of individual microscope images 20. The size of the individual images depends on the magnification factor set at the microscope unit 1. The smaller the magnification factor, the larger the section of the cell culture 8 covered by the individual image 20, the smaller the number of individual images 20 required for total recording of the cell culture 8 and the larger the step movements to be executed by the xy table 9 in order to bring the next-following image section under the microscope unit.

It is accordingly necessary to match the step movements of the xy table 9 with the magnification factor of the microscope unit 1. This matching is effected by the memory and control unit 4. In this case, each of the recorded individual images 20 is uniquely identifiable in its and y coordinates by the position of the xy table 9. At the same time, the coordinates given inside the individual images 20 of the image points contained therein can simply be linked to the coordinates of the individual image. As a result, each image point in each individual image uniquely specifies a location in the scanned cell culture 8.

By reference to the recorded individual images 20 of the cell culture 8, the first and/or second detection step described further below can be carried out to select the cells and/or cell colonies according to specified parameters.

Alternatively to this, the individual images 20 thus recorded are combined in the image evaluation unit 3a to form an overview image 21 of the entire cell culture 8. This combining is appropriate on the one hand because structures which have been recorded at the edges of the respective individual images 20 are completed to form complete objects. On the other hand, the overview picture 21 allows the user a stepless and continuously executable overview of the scanned cell culture 8. The overview image 21 can be processed for this purpose by image processing software and displayed to the user in various resolution stages on the monitor 4a. In conjunction with the generation of the overview image 21, a matching of the coordinates of the individual images 20 and the coordinates of the image points within adjoining individual images is carried out in order to eliminate overlaps of the same image ranges.

The cell detection, i.e. the automatic identification of cells or cell colonies within the individual images 20 is carried out by means of a shape recognition explained hereinafter. FIG. 7 shows for this purpose an exemplary individual image 20, taken from the overview image 21, with cells 22 and a cell colony 23 contained therein, in the microscope image. A prerequisite for reliable shape recognition of the cells is a sufficiently high contrast between the cells or cell colonies and their background in the microscope image. This can be achieved by various methods in microscopy. A first possibility consists in focussing the optical system of the microscope unit 1 onto the image plane of the cell culture 8 in which the cells are to be expected. In the case of adherent cells, this is the surface of the bottom of the sample vessel of the cell culture. Cells in a semi-solid nutrient medium for example, agar, are usually located on the surface of the agar and can be focussed there.

In the case of cells or cell colonies which can be located inside the cell culture in different image planes, techniques involving the fluorescence labelling of microbiological objects can be used. For this purpose, the cells to be identified are marked with a fluorescence marker whilst light having a corresponding excitation wavelength is irradiated via the illumination system. During image acquisition in the area of the fluorescence wavelength of the marker, the cells or cell colonies are distinguished against a dark background as luminous or light structures which form a sufficient colour contrast.

FIG. 8 shows a further schematic step of the image processing. The left-hand diagram shows an individual image 20 converted into grey tones. Conversion into grey tones is particularly advantageous when the cells stand out sufficiently strongly from the background in the microscope image. Naturally, emphasis of a single colour value of the image or a reduction of the image to one colour value is also possible. Likewise, the colour values of image points of the cells to be detected can be predefined as reference, wherein each individual image point within the individual image 20 is compared with this reference value.

Image points which correspond to predefined reference values, i.e. colour values, grey levels, and similar values are combined in the course of the image processing to form point sets whose shape, size and outline can be analysed. The cells 22 are characterised, for example, by relatively large closed shapes 24 which compactly enclose a specified region of the image, the edges thereof running substantially smoothly. The cell colony 23 on the other hand forms a set of individual smaller closely adjacent structures 25 in an image region. Both shapes can easily be identified within the scope of commonly used image detection routines.

On the basis of the identified shapes, further image processing steps are carried out in which the position of the shapes and their mutual distances from one another are calculated. The determination of the position is important for the subsequent removal of the cells or cell colony, the determination of the distance is necessary in order to specify whether the cell or cell colony found must be removed by a single removal process or together with other adjacent cells of the cell culture.

FIG. 9 shows an example for the determination of position and distance. The diagram in FIG. 9 uses the result of the image processing shown schematically in FIG. 8. In the example shown here, a shape centre of gravity S1, S2 or S3 is calculated for each set of image points pertaining to the identified shape, i.e. cell or cell colony. The mode whereby this calculation is made and the size of image section to be selected for its calculations can be specified in advance by the user. As a result, it can be defined inter alia at what point a group of identified cells should be treated as a cell colony or a group of individual cells.

In the example shown here, its own shape centre of gravity S1 or S2 is calculated in each case for the individual shapes 24, each being allocated an x coordinate x1 or x2 and a y coordinate y1 or y2. For the closely adjacent shapes 25, a shape centre of gravity S3 having coordinates x3 and y3 is calculated, which applies to the entire set of these structures and thus lies in an intermediate range of these shapes. With the calculation of the shape centres of gravity and the specification and storage of their coordinates, the cells or cell colonies are uniquely identified in their position. The coordinates are stored together with the image data of the cells and cell colony in a position database and can be uniquely located by retrieving the position database.

For determining the distances of the identified shapes and therefore of the cells or cell colonies, use is made of the determined coordinates, wherein the distances |Sij| between two arbitrary shape centres of gravity Si and Sj and their coordinates (xi; yi) or (xj; yj) are calculated using the Pythagoras relationship $$|Sij| = \sqrt{(xi-xj)^2 + (yi-yj)^2}$$

This calculation can be made automatically as part of the image processing if the determined cells or cell colonies can be found close to one another within previously specified limits. In addition, it is naturally possible for a manual distance calculation to be made by the user as part of editing the position database. In this case, means for an interactive graphical user guidance and image editing are used on the software side in which in particular individual cells can be marked by a mouse click and then the distance between the marked cells is calculated by the image processing program.

The standard image processing software used has extensive possibilities for further documentation of the detection images and results such as graphical evaluations, report generator etc. A continuous documentation of the process is therefore possible.

In a second detection step, it is possible to study the particles already identified with regard to further parameters. In this analysis, the complete starting plate is no longer scanned but only the regions where interesting cell material was found in the first analysis step. This optimises the execution time and in the case of a fluorescence analysis, also the illumination time of the sample with fluorescence light, which should be kept to a minimum to prevent bleaching of the sample. The second detection step can consist of an arbitrary number of individual steps, each of which can be taken up with other types of exposure. Thus, many different fluorescence channels and excitation wavelengths can be scanned and evaluated in this second detection. The software in this case only collects particle data, which are less data-intensive than image data.

At the end of this second detection step, all the data obtained are inserted in the already available particle list for the corresponding original particles. As a result, a corresponding overlapping effect is obtained so that the data from the first analysis can be compared with the data of the second analysis for the same particle. Thus, for example, the quotient of fluorescence area (area, second analysis) divided by the area of the bright-field particle (area, first analysis) yields a quality feature for the antibody production (the lighter and larger the fluorescence signal for the smaller bright field colony, the more this colony produces antibodies).

This particle list can furthermore be filtered logically by means of the presence or the absence of individual fluorescence or bright-field signals. Moreover, the user has the possibility of filtering particles by means of a two-dimensional scatter diagram. In this case, two different particle values from the result table are imaged with respect to one another.

When the table is completely filtered, this list can either be harvested automatically or individually with line accuracy. The AVISO robot control software is responsible for carrying out the actual harvesting process which starts the process in response to a signal from the image processing software. The image processing software in this case takes over the positioning of the cross table and ensure that in each case, the next object to be harvested is located exactly centred in the field of view of the camera so that the harvesting tool which had previously been calibrated to this position, encounters the cells and can pick them.

Communication between the two software components takes place bidirectionally. This includes the image processing software sending information such as particle diameter or position index when using a multi-well plate to the robot control before beginning the harvesting process. As a result, the sequence control is put into a position where the harvesting process can be carried out flexibly for the respective harvesting candidates. A typical application here is the use of automatically changeable cannulas and/or capillaries of different shape, size and material to take into account the different sizes of the particles and achieve optimum harvesting results. It is also possible to have harvested cells deposited in the dispensing container sorted according to classes (density, fluorescence, . . . ) which can be enormously valuable for downstream processes. Independently of this, after each harvesting process the image processing software obtains the information on which container and at which position in this container the robot controller has deposited the cell(s), thus ensuring complete logging of the entire process.

Particles whose size exceeds the usable cannula diameter can be successively harvested in parts. Dissolving out only parts of a colony (e.g. undifferentiated stem cells surrounded by differentiating ones) is also possible.

The colony, partial colony or individual cell to be harvested in each case is positioned by the microscope cross table in the optic axis of the microscope. An image of the particle before harvesting is recorded and stored. The same takes place after harvesting as evidence of the successful harvesting. Both images are allocated to the corresponding well of the target vessel for this particle so that precisely this particle in this well is documented for the further investigation.

The coordinates of the cells or cell colonies are now used for removing the cells. For this purpose, the harvesting module is moved over the cell culture 8 as described, whereby the xy table 9 approaches each coordinate and lowers the harvesting module 5 of the tool head 10 with the removal tool 10a at the corresponding coordinate and activates the cell removal.

FIG. 10 shows the fundamental sequence of the automated cell harvesting using the device. At the beginning of the process, a definition of the identification and harvesting parameter takes place. By reference to these parameters, the scanning process is then carried out with simultaneous identification of the cells and/or cell colonies.

The data determined therefrom are stored in a results list with cells and/or cell colonies found. The cells and/or cell colonies found can be further filtered from this results list. This is effected with by a manual reprocessing, i.e. removing/adding/separating/combining of cells and/or cell colonies or by applying additional analysis functions to the cells and/or cell colonies found. For example, an examination for different fluorescences can be made.

After the cells and/or cell colonies have been selected in this way, the automatic harvesting can be started. For this, it must firstly be analysed whether the cell and/or cell colony can be harvested with the present removal tool on account of its size and whether other cells and/or cell colonies are located in the withdrawal region of the removal tool. If harvesting is possible, this is then carried out. The result of the harvesting is stored in the results list of the harvesting including documentation of the before/after images. Then, the analysis of the harvesting possibility described above is carried out anew for the next cell and/or cell colony, if possible followed by harvesting.

If harvesting is not possible, the reason for this is firstly determined and the result is stored in the results list of the harvesting including documentation of the before/after images. This is again followed by the analysis described above for the next cell and/or cell colony, if possible followed by harvesting.

After harvesting the last cell and/or cell colony, the process is automatically ended.

FIG. 11 shows a receptacle 32 which is attached to the tool head 10. The receptacle 32 comprises an outer cone 26 which is graded in steps 28. This outer cone 26 receives a removal tool 10a which is a tip here and has an inner cone 27 which forms a counterpart to the outer cone 26 of the receptacle 32. Due to the meshing of the outer cone 26 of the receptacle 32 and the inner cone 27 of the removal tool 10a, a non-positive detachable connection is formed between the receptacle 32 and the removal tool 10a.

FIG. 12 shows an alternative embodiment of a receptacle 32. The receptacle 32 here comprises an inner cone 31. This inner cone 31 receives a removal tool 10a which is a capillary here and comprises an outer cone 30 which forms a counterpart to the inner cone 31 of the receptacle 32. Due to the meshing of the inner cone 31 of the receptacle 32 and the outer cone 30 of the removal tool 10a, a non-positive detachable connection is formed between the receptacle 32 and the removal tool 10a.

By using different conical receptacles 32, matched in their size and design, for the very diverse, frequently newly developed consumables used, in the form of exchangeable cannulas, a largely uniform tool geometry can be retained.

The conical receptacle 32 results in self-centring of the consumables (cannulas) partially to be positioned with high precision when received by the tool. Due to the high stability of the conical receptacle 32 and the uniform force distribution, the application of relatively high transverse forces to the exchangeable capillaries is possible, e.g. during scraping without loss of positioning accuracy or loosening of the exchangeable cannulas in the receptacle 32. By using a thickening below the conical receptacle 32 on the tool head, the exchangeable cannulas can be removed from the tool again by means of a simple stripping device, not shown, to allow receipt of the next exchangeable cannula.

At the same time, this collar also serves to allow the magazining of even sensitive consumables such as, for example, small-diameter glass capillaries, to feed these in large numbers to the automated process. Usually racks of 96 are used for this purpose.

It is possible to use various conical receptacles 32 for adapting a wide range of automatedly exchangeable capillaries and cannulas of very diverse size, shape and materials on a tool of the same type for the purposes of the automated investigation and separation of individual cells or cell colonies.

Capillaries of glass, metal or ceramic can be used.

REFERENCE LIST

1 Microscope unit
1a Deflecting prism
1b Lens system
2 Image recording unit
3 PC
3a Image evaluation unit
4 Control and memory unit
4a Monitor, display
5 Harvesting module
5a Lifting column
5b Displacement drive
6 Illumination
7 Illumination filter
8 Cell culture
9 xy table
10 Tool head
10a Removal tool
11 Separating battery
12 Tip
12a End cone
13 Cloning cup
13a Picking cone
14 Cannula magazine
15 Cannula
16 Exchangeable head
16a Adapter
17 Tip
18 Cannula for positionally fixed individual cell
18a Fluid level
19 Calibrating image acquisition
20 Individual image
21 Overview image
22 Cell
23 Cell colony
24 Cell shape
25 Cell colony structure
S1 First shape centre of gravity
S2 Second shape centre of gravity
S3 Third shape centre of gravity
x1 First x coordinate
x2 Second x coordinate
x3 Third x coordinate
y1 First y coordinate
y2 Second y coordinate
y3 Third y coordinate
26 Outer cone
27 Inner cone
28 Step
30 Outer cone
31 Inner cone
32 Receptacle

The invention claimed is:

1. A method for automated removal of cells and/or cell colonies from a cell culture comprising:
scanning a vessel containing a cell culture;
executing a first detection step during said scanning step for selecting cells and/or cell colonies within the cell culture with reference to corporeal and/or physical parameters;
detecting position data and storing the detected position data of the selected cells and/or cell colonies in a position database;
scanning again the vessel in at least one region in which cells and/or cell colonies having the corporeal and/or physical parameters were found in the first detection step;
executing at least one second detection step for detecting at least one further parameter of the cells and/or cell colonies only in the at least one region in which cells and/or
cell colonies having the corporeal and/or physical parameters, were found in the first detection step;
creating comparative data from the data of the first and second detection steps and allocating the comparative data to the position data;
selecting cells and/or cell colonies having a plurality of specified properties with reference to the comparative data with the corporeal and/or physical parameters and by reference to specific criteria for different cell types;
transferring the position data linked to the comparative data from the position database to a harvesting unit;
removing selected cells and/or cell colonies from the cell culture by means of a removal tool of the harvesting unit; and
recording at least partial images of the cell culture during the scanning steps, wherein at least one of the first and second detection steps are carried out with reference to the partial images, wherein at least one image is recorded prior to removal of the selected cells and/or cell colonies from the cell culture, and at least one image is recorded after removal of the selected cells and/or cell colonies from the cell culture.

2. The method according to claim 1, further comprising the steps of:
providing an xy table is provided as a support for the vessel of the cell culture, wherein the scanning step includes moving the vessel with the xy table.

3. The method according to claim 1, wherein:
said recording step is further defined as recording an entirety of the partial images covering the cell culture during the scanning step, and wherein the method further comprises the step of:
combining image data of the partial images in an image evaluation unit to form image data of an overview image of the cell culture.

4. The method according to claim 3, further comprising the step of:
making a determination of a shape centre of gravity of cells and/or cell colonies detected during the step of detecting position data by calculating a shape centre of gravity from each set of image points which pertain to the identified shape of the cell or cell colony, wherein coordinates of the shape centre of gravity are stored as the position data for the identified shape in the position database.

5. The method according to claim 4, further comprising the step of:
   determining at least one distance between forms identified during the step of making a determination, wherein the determined distance |Sij| between two shape centres of gravity Si and Sj and their coordinates (xi; yi) or (xj; yj) are calculated using the Pythagoras relationship
   $$|Sij|=\sqrt{[(xi-xj)^2+(yi-yj)^2]}.$$

6. The method according to claim 5, further comprising the step of:
   displaying image data obtained during at least one of the scanning steps, the making a determination of a shape centre step, and the detecting position data step in real-time on a monitor.

7. The method according to claim 1, wherein the second detection step includes recording different parameters with different fluorescence channels and excitation wavelengths.

8. The method according to claim 1, further comprising the step of:
   providing a first interactive selection list, wherein the interactive selection list allows an automated selection of cells and/or cell colonies and also a manual viewing of the position database and an examination and selection of the cells and/or cell colonies found in an automated manner.

9. The method according to claim 8, wherein the providing step is further defined as:
   providing the first interactive selection list, wherein the first interactive selection list contains at least coordinates of shape centres of gravity and image data and/or data from the first detection step.

10. The method according to claim 1, further comprising the step of:
    providing an interactive scatter diagram allowing an automated selection of the cells and/or cell colonies.

11. The method according to claim 10, wherein the providing step is further defined as:
    providing a first interactive selection list to contain at least the data from the second detection step and/or the comparative data.

12. The method according to claim 1, further comprising the step of: selecting the cells and/or cell colonies by logic filters.

13. The method according to claim 1, wherein said removing step is further defined as:
    picking of cells and/or cell colonies from a semisolid nutrient substrate being one of agar or methyl cellulose by:
    taking up a cannula tip;
    positioning the tip over a cell and/or cell colony and enclosing the cell and/or cell colony; and
    aspirating the cell and/or cell colony and the nutrient substrate in the vicinity of the cell and/or the cell colony into the tip.

14. The method according to claim 13, wherein the aspirating step further comprises the step of
    harvesting a cell colony whose size exceeds the usable diameter of the cannula tip successively in parts.

15. The method according to claim 13, further comprising the step of:
    dissolving individual parts out from a cell colony with the aid of the tip.

16. The method according to claim 13, further comprising the step of:
    dissolving individual regions out from solid cell groups.

17. The method according to claim 1, wherein said removing step is further defined as:
    picking of positionally fixed individual cells and/or individual colonies by:
    filling a capillary with a fluid being one of air and a liquid in a calibrated quantity;
    positioning the capillary opening above an individual cell and/or individual colony; and
    aspirating a medium in the vicinity of the individual cell and/or individual colony into the capillary, wherein the individual cell and/or individual cell colony is picked into the capillary.

18. The method according to claim 17, wherein the aspirating step further comprises the step of:
    harvesting a cell colony whose size exceeds the usable diameter of the capillary successively in parts.

19. The method according to claim 17, further comprising the step of:
    dissolving individual parts out from a cell colony with the aid of the capillary.

20. The method according to claim 17, further comprising the step of:
    dissolving individual regions out from solid cell groups.

21. The method according to claim 1, further comprising the steps of: sorting the cells and/or cell colonies by:
    depositing the cells and/or cell colonies in a depositing container;
    detecting the position data of the deposited cell and/or cell colony; and
    processing the position data.

* * * * *